United States Patent [19]

Battelli et al.

[11] Patent Number: 4,670,262
[45] Date of Patent: Jun. 2, 1987

[54] NOVEL PHARMACOLOGICAL COMPOSITIONS BASED ON CISPLATINUM AND METHOD FOR OBTAINING SAME

[75] Inventors: Gaetano Battelli, Monza; Diego Oldani, Robecco sul Naviglio; Alessandro Rigamonti, Milan, all of Italy

[73] Assignee: Farmitalia Carlo Erba S.p.A., Milan, Italy

[21] Appl. No.: 738,436

[22] Filed: May 28, 1985

Related U.S. Application Data

[63] Continuation of Ser. No. 532,382, Sep. 15, 1983, abandoned.

[30] Foreign Application Priority Data

Sep. 23, 1982 [IT] Italy ............................... 23396 A/82

[51] Int. Cl.$^4$ .............................................. A61K 33/24
[52] U.S. Cl. ..................................................... 424/131
[58] Field of Search ........................................ 424/131

[56] References Cited

U.S. PATENT DOCUMENTS

| | | | |
|---|---|---|---|
| 3,892,790 | 7/1975 | Tobe et al. | 514/492 |
| 3,904,663 | 9/1975 | Tobe et al. | 514/492 |
| 4,053,587 | 10/1977 | Davidson et al. | 424/131 |
| 4,255,417 | 3/1981 | Bohm et al. | 424/131 |
| 4,273,755 | 6/1981 | Rhoda et al. | 424/131 |
| 4,302,446 | 11/1981 | Kaplan et al. | 424/131 |
| 4,451,447 | 5/1984 | Kaplan et al. | 424/131 |

OTHER PUBLICATIONS

See–Lasley et al., "Manual of Oncology Therapeutics", The C. V. Masby Company, pp. 189–190 (1981).

Primary Examiner—Jerome D. Goldberg
Attorney, Agent, or Firm—Oblon, Fisher, Spivak, McClelland & Maier

[57] ABSTRACT

The present invention relates to the preparation of sterile and stable freeze-dried forms of Cisplatinum containing from 10 to 50 mg of active ingredient, which can be obtained on an industrial scale and which have particular characteristics of facility and rapidity of dissolution which permit them to be used in a more advantageous and rational manner in antitumor chemotherapy, as compared with the freeze-dried forms of Cisplatinum presently on the market.

These particular characteristics are achieved as the result of employing special ingredients in respect of formulation (concentration of the solution to be freeze-dried, introduction of alcohols, adjustment of the pH of the solution to an appropriate value), and as the result of using a manufacturing technique having as its final stage the freeze-drying of Cisplatinum in a water-alcoholic medium.

The manufacturing method, and in particular the freeze-drying process, have shown themselves to be economically advantageous, and have made it possible to overcome the very considerable problems connected with the freeze-drying of Cisplatinum in aqueous medium (breakage of containers, very low yields), as well as to obtain preparations perfectly adapted to be used therapeutically by intravenous administration.

14 Claims, No Drawings

NOVEL PHARMACOLOGICAL COMPOSITIONS BASED ON CISPLATINUM AND METHOD FOR OBTAINING SAME

This is a continuation of application Ser. No. 532,382, filed Sept. 15, 1983, now abandoned.

The present invention relates to the preparation of sterile and stable freeze-dried forms of Cisplatinum, containing from 10 mg to 50 mg of the active substance, obtained from water-alcoholic solutions and intended, after reconstitution with sterile water for injection, to be used parenterally in the chemotherapy of cancer in man.

The inorganic complexes of platinum are a very large class of substances possessing antitumor activity. The antibiotic activity of such complexes was first discovered in 1965 by Rosenberg et al, who demonstrated that they inhibit cell division in cultures of *Escherichia coli* (B. Rosenberg et al, Nature, 205, 698–699, 1965). Subsequently, attention centered on the ability of these compounds to block the proliferation of certain experimental tumors induced in laboratory animals. It was also observed that Cis-Platinum (II) Diamminedichloride was very active on mouse Sarcoma 180 and mouse Leukemia 1210 (B. Rosenberg et al, Nature, 222, 385–386, 1969). Structurally, Cis-Platinum (II) Diamminedichloride can be described as a complex in which the central atom is an atom of platinum, which is bound to chlorine atoms and amino groups disposed in cis or trans configuration:

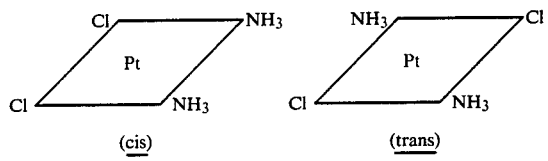

(cis)        (trans)

The cis-isomer is the biologically active form and is obtained according to the following scheme of synthesis (G. B. Kaufmann et al, "Inorganic Synthesis", 293–245, McGraw-Hill Book Co., Inc., New York, 1963):

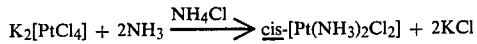

A. Atilla Hincal and co-workers, in Journal of the Parenteral Drug Association, Vol. 33, No. 3, pages 107 to 116 (1979), assessed the chemical stability of Cis-Platinum (II) Diamminedichloride in aqueous solution in the presence of different solutes (dextrose, mannitol, sodium chloride, sodium bicarbonate). These researchers noted that Cisplatinum is stabilized in aqueous solution by the presence of chloride ions. In particular, saline solutions having concentrations of sodium chloride of between 0.45% (w/v) and 0.9% (w/v), at room temperature and protected from light, stabilize the aqueous solutions of Cisplatinum for at least 24 hours. A. Rossef et al, in Cancer, 30, 1451–1456 (1972), describe the results obtained with Cisplatinum in the treatment of 31 cases of human tumors. These researchers used a formulation of freeze-dried active substance supplied by the National Cancer Institute and manufactured by Ben Venue Laboratories, containing 10 mg of Cisplatinum, 90 mg of sodium chloride, and 100 mg of mannitol. This substance was redissolved with 8 to 10 ml of sterile water for injection.

Further information on the chemical characteristics of Cisplatinum and a related freeze-dried pharmaceutical dosage form is reported on pages 1 to 5, 31 and 32 of the publication entitled "Clinical Brochure, Cis-Platinum (II) Diamminedichloride (MSO-119875)" by H. Handelsman et al of the Section of Pharmacology and Therapy of the National Cancer Institute (up-dated version of August 1974).

SUBJECT MATTER OF THE INVENTION

The present invention relates to the preparation in vials of sterile freeze-dried doses of Cisplatinum obtained from water-alcoholic solutions, stable and usable parenterally in antiblastic chemotherapy, the preparation being such as to obviate certain difficulties previously encountered in the production of industrial batches of freeze-dried Cisplatinum.

The freeze-dried products obtained according to the procedures of the present invention may contain from 10 to 50 mg of Cisplatinum, from 45 to 450 mg of sodium chloride, from 100 to 1500 mg of an inert and nontoxic excipient such as mannitol, and hydrochloric acid for adjustment of pH. They also contain residues of nontoxic alcohols at totally innocuous concentrations (0.01%–0.05%), such as will not give rise to clinical complications at the time of administration of the product.

These products are used after first dissolving them with sterile water for injection (from 10 to 50 ml), the dissolution times being less than one minute, thereby obtaining clear solutions having a concentration of 1 mg of Cisplatinum per milliliter of water for injection.

It is known that, since the solubility of Cisplatinum in water is only approximately 1 mg/ml at room temperature, the manufacture of freeze-dried pharmaceutical dosage forms, containing for example 25 or 50 mg of active ingredient, necessarily requires freeze-drying from considerable volumes of solution (25 and 50 ml respectively), such as make the entire process somewhat critical both economically (very lengthy freeze-drying times, extensive breakage of vials, very low yields) and technologically (difficulty of controlling and dominating the freeze-drying process because of the excessive thicknesses of the product).

The object of the present invention is therefore to provide the technological and formulative conditions adapted to yield sterile and stable freeze-dried forms of Cisplatinum dosed to 50 mg of active ingredient under wholly normal industrial processing conditions, such forms being suitable for therapeutic use by intravenous administration after reconstitution with sterile water for injection.

The above object has been attained by introducing the following innovations:

1. increasing the concentration of Cisplatinum in the solution to be freeze-dried by using a water-alcoholic vehicle, and by treating the solution at a temperature of between 35° and 45° C., and preferably 40° C., such that it is in any case compatible with the chemical stability of the active ingredient. The foregoing has made it possible to obtain concentrations of the order of 1.2 to 2 mg/ml and preferably 1.33 mg/ml;
2. introducing into the formulation alcohols, such as for example ethyl alcohol, isopropyl alcohol, tert-butyl alcohol, at concentrations of between 0.2% (v/v) and 5% (v/v) and preferably of from 0.5% (v/v) to 2% (v/v); and
3. adjusting the pH of the solution to be freeze-dried to values of between 3.2 and 4, and preferably 3.5, with dilute mineral acids such as for example 1N hydrochloric acid.

The increase of the concentration of Cisplatinum in the solution to be freeze-dried has made it possible to reduce the volumes per single container, limiting such volumes to 5 to 7.5 ml of the 10 mg dose; to 12.5 to 18.75 ml for the 25 mg dose; and to 25 to 37.5 ml for the 50 mg dose. The reduction of the volume of the solution has consequently led to less critical process conditions as a result of the decrease of the quantity of water required to be removed during the freeze-drying. The introduction of innocuous alcoholic substances compatible with the chemical nature of Cisplatinum has allowed modification of the eutectic area of the solution. Such introduction has made possible the following:

(a) to obviate breakages of vials during freeze-drying. The breakages can reach as much as 10% and 30% during freeze-drying of aqueous solutions of Cisplatinum in the 25 and 50 mg doses. The total elimination of container breakage has allowed the product to be processed on an industrial scale in wholly safe environmental and hygienic conditions, such as to guarantee the protection of the personnel employed, from the spreading into the environment of freeze-dried active substance and from contact with same when the freeze-dryer is opened. The elimination of breakages has also obviated the need for frequent cleaning of the environment and equipment used for the freeze-drying, while at the same time solving the problem of cross-contamination which would inevitably be encountered in the subsequent processing of other biologically active products.

(b) to reduce the overall freeze-drying times by about 20% with respect to the times normally required during the freeze-drying of similar volumes of aqueous solutions of Cisplatinum. This reduction was made possible by virtue of the low vapor pressure of the alcohols which are liberated during the sublimation from the frozen product in the form of unstable vapors mixed with water vapor, which condense on the cold walls of the condenser.

If it is further considered that the solution to be freeze-dried is concentrated, as stated previously (i.e., 1.2 to 2 mg/ml of Cisplatinum instead of 1 mg/ml), the freeze-drying times are additionally reduced by about another 20%.

The combination of these innovations (presence of alcohols and concentration of the solution) according to the present invention has allowed the Cisplatinum freeze-drying process to be conducted under working conditions and with manufacturing times which are otherwise entirely normal for a freeze-dried pharmaceutical dosage form.

The freeze-dried products obtained under such conditions have a brittle porous structure readily reconstituted with water for injection, with dissolution times of within one minute.

The average times for the industrial freeze-drying process (excluding freezing time) according to the present invention for the 10 mg, 25 mg and 50 mg doses of Cisplatinum are summarized in the following Table:

| Cisplatinum mg/vial | Fill volume (ml) | % (v/v) ethyl alcohol | Freeze-drying time (h) |
|---|---|---|---|
| 10 | 5 to 7.5 | 0.5 to 2 | 13 to 18 |
| 25 | 12.5 to 18.75 | 0.5 to 2 | 18 to 25 |
| 50 | 25 to 37.5 | 0.5 to 2 | 27 to 34 |

The adjustment of the pH of the solution to be freeze-dried to between 3.2 and 4 with 1N hydrochloric acid (unlike what occurs for other specialties on the market, for which the pH is adjusted to 2.3 to 2.7), makes it possible to decrease the quantity of mineral acid, which in freeze-drying has a corrosive action on the materials of which the plant equipment is made.

The reduction of the quantity of hydrochloric acid does not in any case adversely affect the chemical stability of the product and has, moreover, allowed freeze-dried products to be obtained which, after reconstitution with water for injection, provide solutions of Cisplatinum having a pH of between 4 and 6.5, and thus closer to physiological values.

Starting from solutions of Cisplatinum prepared according to the variants introduced according to the present invention, there are obtained freeze-dried products dosed respectively to 10, 25 and 50 mg of Cisplatinum per vial, which remain stable over time (the expiration dating allotted is at least two years) and which can be stored for their entire period of viability at room temprature. During such storage period, the freeze-dried products maintain unvaried their initial characteristics, which are summarized below:

1. good physical and chemical stability of the reconstituted solution of concentration of 1 mg/ml of Cisplatinum, even after 24 hours at room temperature and exposure to environmental light (appearance, color, pH, assay);
2. dissolution time of between thirty seconds and one minute. Dissolution is performed by adding sterile water for injection (10 ml of water for injection for the freeze-dried product dosed to 10 mg; 25 ml for the freeze-dried product dosed to 25 mg; and 50 ml for the freeze-dried product dosed to 50 mg) so as to obtain a solution having a concentration of 1 mg/ml of Cisplatinum.

The extreme facility and rapidity of dissolution of the freeze-dried Cisplatinum products obtained from water-alcoholic solutions (dissolution times between 30 seconds 1 minute) provide a guarantee and a safety factor when used in hospitals, where these preparations are employed by the intravenous route in antiblastic chemotherapy. The rapidity and ease of redissolving the preparations allow one to eliminate the risks connected with the intravenous administration of solutions of Cisplatinum containing undissolved crystals as a result of insufficient manual agitation of the vials when the solvent is added.

By comparison with the freeze-dried forms of Cisplatinum until now available (time required for solution up to three minutes), the freeze-dried forms of Cisplatinum obtained from water-alcoholic solutions and prepared according to the present invention, allow a distinct improvement of the characteristics of solubility of the active ingredient, bringing the times of agitation during the reconstitution of the products to values which are well within the norm for a freeze-dried pharmaceutical dosage form (from 30 seconds to one minute)

The following detailed examples will serve still further to illustrate this invention:

EXAMPLE 1

| 10 mg freeze-dried Cisplatinum product | |
|---|---|
| Formulation | per vial |
| Cis-Platinum (II) Diamminedichloride | 0.010 g |
| Sodium chloride USP | 0.045 g |
| Mannitol USP | 0.300 g |
| 1N Hydrochloric acid sufficient to adjust to pH = 3.5 | |
| Isopropyl alcohol | 0.015 ml |
| Water for injections (USP) sufficient to make | 7.500 ml |

1. In 90% of the water for injection, deaereated by bubbling in of nitrogen, dissolve the sodium chloride under agitation.
2. Heat the resulting solution to 40° to 45° C. and dissolve the Cis-Platinum (II) Diamminedichloride under bubbling in of nitrogen and vigorous agitation. Perform this operation protected from light. In the subsequent processings, also keep the solution protected from light.
3. Slowly cool the solution to 28°/30° C. and dissolve the mannitol.
4. Adjust the pH of the solution to 3.5 with 1N hydrochloric acid.
5. Under agitation, add the isopropyl alcohol and make up to the final volume.
6. Aseptically filter the solution through a membrane filter of pore size 0.22 u.
7. Aseptically dispense the solution into colorless, sterile glass filters, type I, capacity 20 ml, to a volume of 7.5 ml per vial.
8. Freeze the vials at −45° C.
9. Proceed to freeze-drying, heating the shelves of the freeze-dryer system to 40° C. Limit the time employed for the final drying of the product at 25°/35° C. (preferably 30° C.) to 3 to 6 hours, and preferably 4 hours.
10. Stopper the freeze-dried vials with sterile stoppers made of elastomeric material, preferably halobutylic rubbery material (a mixture in chlorobutylic rubbrr type PH 21/50, manufactured by Pharmagummi), and seal with sterile aluminum caps.

Freeze-drying time (excluding freezing time): 18 hours

Dissolution time of the freeze-dried product using 10 ml of sterile water for injection: 30 seconds.

EXAMPLE II

| 25-mg freeze-dried Cisplatinum product | |
|---|---|
| Formulation | per Vial |
| Cis-Platinum (II) Diamminedichloride | 0.025 g |
| Sodium Chloride USP | 0.200 g |
| Mannitol USP | 0.600 g |
| 1N Hydrochloric acid sufficient to adjust to pH = 3.2 | |
| 96% Ethyl alcohol | 0.375 ml |
| Water for injection (USP) sufficient to make | 18.750 ml |

Preparation is similar to that described above for Example 1, excluding points 4, 5 and 7, which are modified as follows:

4. Adjust the pH of the solution to 3.2 with 1N hydrochloric acid.
5. Under agitation, add the 96% ethyl alcohol and make up to the final volume.
7. Aseptically dispense the solution into sterile, colorless glass vials, type I, capacity 50 ml, to a volume of 18.75 ml per vial.

Freeze-drying time (excluding freezing time): 25 hours

Dissolution time of the freeze-dried product using 25 ml of sterile water for injection: 1 minute.

EXAMPLE III

| 50-mg freeze-dried Cisplatinum product | |
|---|---|
| Formulation | per vial |
| Cis-Platinum (II) Diamminedichloride | 0.050 g |
| Sodium chloride USP | 0.225 g |
| Mannitol USP | 1.500 g |
| 1N Hydrochloric acid sufficient to adjust to pH = 4 | |
| Tert-Butyl alcohol | 0.375 ml |
| Water for injection (USP) sufficient to make | 37.500 ml |

Preparation is similar to that described above for Example 1, except for points 4, 5 and 7, which are modified as follows:

4. Adjust the pH of the solution to 4 with 1N hydrochloric acid.
5. Under agitation, add the tert-butyl alcohol and make up to the final volume.
7. Aseptically dispense the solution into sterile colorless glass vials, type I, capacity 100 ml, to a volume of 37.5 ml per vial.

Freeze-drying time (excluding freezing time): 33 hours

Dissolution time of the freeze-dried product using 50 ml of sterile water for injection: 30 seconds.

EXAMPLE IV

| 10-mg freeze-dried Cisplatinum product | |
|---|---|
| Formulation | per Vial |
| Cis-Platinum (II) Diamminedichloride | 0.010 g |
| Sodium chloride USP | 0.090 g |
| Mannitol USP | 0.150 g |
| 1N Hydrochloric acid sufficient to adjust to pH = 3.5 | |
| 96% Ethyl alcohol | 0.025 ml |
| Water for injection (USP) sufficient to make | 5.000 ml |

Preparation is similar to that described above for Example 1, except for points 5 and 7, which are modified as follows:

5. Under agitation, add the 96% ethyl alcohol and make up to the final volume.
7. Aseptically dispense the solution into sterile, colorless amber glass vials, type I, capacity 20 ml, to a volume of 5 ml per vial.

Freeze-drying time (excluding freezing time): 15 hours

Dissolution time of freeze-dried product using 10 ml of sterile water for injection: 1 minute.

EXAMPLE V

| 25-mg freeze-dried Cisplatinum product | |
|---|---|
| Formulation | per Vial |
| Cis-Platinum (II) Diamminedichloride | 0.025 g |
| Sodium chloride USP | 0.120 g |
| Mannitol USP | 0.750 g |

| 25-mg freeze-dried Cisplatinum product | |
|---|---|
| Formulation | per Vial |
| 1N Hydrochloric acid sufficient to adjust to pH = 3.5 | |
| 96% Ethyl alcohol | 0.125 ml |
| Water for injection (USP) sufficient to make | 12.500 ml |

Preparation is similar to that described above for Example 1, except for points 5, 7 and 10, which are modified as follows:

5. Under agitation, add the 96% ethyl alcohol and make up to the final volume.

7. Aseptically dispense the solution into sterile, colorless glass vials, type I, capacity 50 ml, to a volume of 12.5 ml per vial, and apply chlorobutyl rubber stoppers; then freeze.

10. Close the freeze-dried vials directly in the chamber using the internal-stoppering device. Discharge the vials and seal with sterile aluminum caps.

Freeze-drying time (excluding freezing time): 20 hours

Dissolution time of the freeze-dried product using 25 ml of sterile water for injection: 1 minute.

EXAMPLE VI

| 50-mg freeze-dried Cisplatinum product | |
|---|---|
| Formulation | per Vial |
| Cis-Platinum (II) Diamminedichloride | 0.050 g |
| Sodium chloride USP | 0.450 g |
| Mannitol USP | 0.500 g |
| 1N Hydrochloric acid sufficient to adjust to pH = 3.2 | |
| Isopropyl alcohol | 0.187 ml |
| Water for injection (USP) sufficient to make | 37.500 ml |

Preparation is similar to that described above for the Example 1, except for points 4 and 7, which are modified as follows:

4. Adjust the pH of the solution to 3.2 with 1N hydrochloric acid.

7. Aseptically dispense the solution into sterile, colorless glass vials, type I, capacity, 100 ml to a volume of 37.5 ml per vial.

Freeze-drying time (excluding freezing time): 32 hours

Dissolution time of the freeze-dried product using 50 ml of sterile water for injection: 30 seconds.

What is claimed is:

1. A composition, comprising from 10 mg to 50 mg of Cis-platinum(II) diaminedichloride, from 45 mg to 450 mg of sodium chloride, from 100 mg to 1500 mg of mannitol, and from 0.01% to 0.05% of a non-toxic alcohol which is at least one member selected from the group consisting of ethyl alcohol, isopropyl alcohol and tert-butyl alcohol.

2. The composition of claim 1, said composition having a dissolution time of from 30 seconds to 1 minute in a pharmaceutically acceptable carrier, and a stability of at least two years when stored at room temperature.

3. The composition of claim 1, said composition comprising from 10 mg to 25 mg of Cis-platinum(II) diaminedichloride.

4. The composition of claim 1, said composition comprising from 25 mg to 50 mg of Cis-platinum(II) diaminedichloride.

5. A pharmacological composition, comprising a pharmaceutically effective amount of the composition of claim 1 in combination with a pharmaceutically acceptable carrier.

6. The pharmacological composition of claim 5, comprising from 10 mg to 25 mg of Cis-platinum(II) diaminedichloride.

7. The pharmacological composition of claim 5, comprising from 25 mg to 50 mg of Cis-platinum(II) diaminedichloride.

8. A process for producing the composition of claim 1, said process comprising:
(i) preparing a solution containing from 10 mg to 50 mg of Cis-platinum(II) diaminedichloride, from 45 mg to 450 mg of sodium chloride, from 100 mg to 1500 mg of mannitol, and from 0.2% (v/v) to 5% (v/v) of a non-toxic alcohol which is at least one member selected from the group consisting of ethyl alcohol, isopropyl alcohol and tert-butyl alcohol;
(ii) heating the said solution to a temperature of between 35° C. and 45° C., and adjusting the pH of the solution to a value of between 3.2 and 4; and
(iii) freeze-drying the said solution.

9. A process for producing a Cis-platinumm (II) diaminedichloride composition, said process comprising:
(i) freeze-drying a solution having a volume of from 5 ml to 37.5 ml, said solution comprising (a) from 10 mg to 50 mg of Cis-platinum(II) diaminedichloride, from 45 mg to 450 mg of sodium chloride, from 100 mg to 1500 mg of mannitol, from 0.2% (v/v) to 5% (v/v) of a non-toxic alcohol which is at least one member selected from the group consisting of ethyl alcohol, isopropyl alcohol, and tert-butyl alcohol, and water; and
(ii) recovering the said Cis-platinum(II) diaminedichloride composition.

10. The process of claim 9, comprising using from 10 mg to 25 mg of Cis-platinum(II) diaminedichloride.

11. The process of claim 9, comprising using from 25 mg to 50 mg of Cis-platinum(II) diaminedichloride.

12. The process of claim 9, comprising adjusting the pH of the said solution, prior to freeze-drying, to a pH value of between 3.2 and 4.0.

13. The process of claim 12, comprising adjusting the said pH value with a dilute mineral acid.

14. The process of claim 12, comprising adjusting the said pH value with hydrochloric acid.

* * * * *

UNITED STATES PATENT AND TRADEMARK OFFICE
CERTIFICATE OF CORRECTION

PATENT NO. : 4,670,262
DATED : JUNE 2, 1987
INVENTOR(S) : GAETANO BATTELLI ET AL

It is certified that error appears in the above-identified patent and that said Letters Patent is hereby corrected as shown below:

Column 4, line 30, delete "temprature" and insert

--temperature--.

Column 5, line 34, after "glass" insert --vials--;

line 44, delete "rubbrr" and insert --rubber--.

Column 6, lines 54-55, delete the word "color-less".

Signed and Sealed this

Twenty-third Day of February, 1988

Attest:

DONALD J. QUIGG

Attesting Officer      Commissioner of Patents and Trademarks